(12) United States Patent
Mukaide et al.

(10) Patent No.: US 9,101,322 B2
(45) Date of Patent: Aug. 11, 2015

(54) X-RAY IMAGING APPARATUS AND IMAGING METHOD

(75) Inventors: Taihei Mukaide, Atsugi (JP); Nao Nakatsuji, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 792 days.

(21) Appl. No.: 13/376,576

(22) PCT Filed: Jun. 20, 2011

(86) PCT No.: PCT/JP2011/064606
§ 371 (c)(1),
(2), (4) Date: Dec. 6, 2011

(87) PCT Pub. No.: WO2012/008287
PCT Pub. Date: Jan. 19, 2012

(65) Prior Publication Data
US 2012/0148023 A1 Jun. 14, 2012

(30) Foreign Application Priority Data

Jul. 12, 2010 (JP) ................................ 2010-158133

(51) Int. Cl.
*G01N 23/04* (2006.01)
*A61B 6/00* (2006.01)
(Continued)

(52) U.S. Cl.
CPC .............. *A61B 6/484* (2013.01); *A61B 6/4035* (2013.01);
(Continued)

(58) Field of Classification Search
CPC ..... G01N 23/04; G01N 23/046; G01N 23/20; G01N 2223/419; A61B 6/0306; A61B 6/482; A61B 6/484; A61B 6/504; A61B 6/488; A61B 6/4035; A61B 6/4261; G21K 1/043; G21K 1/046; G21K 2207/005
USPC ............................................. 378/62, 19, 98.8
See application file for complete search history.

(56) References Cited

U.S. PATENT DOCUMENTS 4,651,002 A 3/1987 Anno
6,483,891 B1 * 11/2002 Lazarev et al. ................ 378/37
8,509,382 B2 * 8/2013 Mukaide et al. ............... 378/62

FOREIGN PATENT DOCUMENTS

| CN | 101495853 A | 7/2009 |
|---|---|---|
| CN | 102187207 A | 9/2011 |
| CN | 102272860 A | 12/2011 |
| CN | 102458254 A | 5/2012 |
| CN | 102713679 A | 10/2012 |
| JP | 61143038 A | 6/1986 |
| JP | 63082628 A | 4/1988 |
| JP | 2003018463 A | 1/2003 |

(Continued)

OTHER PUBLICATIONS

Japanese Office Action issued Feb. 4, 2014 for counterpart application JP 2010-158133, and English-language translation thereof is attached.

*Primary Examiner* — Irakli Kiknadze
(74) *Attorney, Agent, or Firm* — Canon USA Inc. IP Division

(57) ABSTRACT

An X-ray imaging apparatus and an imaging method capable of acquiring an image of a test object associated with a phase shift in consideration of X-ray absorption is provided. A splitting element configured to spatially split an X-ray into multiple X-ray beams is provided. A shielding unit including a plurality of shielding elements configured to block part of an X-ray acquired by the splitting element is provided. Part of X-ray beams detected at the first detection pixels is blocked by the shielding elements. The X-ray beams detected by the second detection pixels adjoining the first detection pixels are not blocked by the shielding elements.

16 Claims, 7 Drawing Sheets

(51) Int. Cl.
*G01N 23/20* (2006.01)
*G21K 1/04* (2006.01)

(52) U.S. Cl.
CPC ............ *A61B 6/4291* (2013.01); *G01N 23/046* (2013.01); *G01N 23/20* (2013.01); *G21K 1/043* (2013.01); *G21K 1/046* (2013.01); *G01N 2223/419* (2013.01); *G21K 2207/005* (2013.01)

(56) References Cited

FOREIGN PATENT DOCUMENTS

| | | |
|---|---|---|
| JP | 2010502977 A | 1/2010 |
| WO | 2008/029107 A2 | 3/2008 |
| WO | 2009/115966 A1 | 9/2009 |
| WO | 2010/147125 A1 | 12/2010 |

\* cited by examiner

X-RAY IMAGING APPARATUS AND IMAGING METHOD

TECHNICAL FIELD

The present invention relates to an X-ray imaging apparatus and an imaging method.

BACKGROUND ART

A non-destructive inspection method using X-ray is applied to various areas ranging from industrial use to medical use. An X-ray beam is an electromagnetic wave having a wavelength between approximately 1 pm ($10^{-12}$ m) to approximately 10 nm ($10^{-8}$ m). An X-ray beam having a shorter wavelength is referred to as a hard X-ray beam, and an X-ray having a longer wavelength is referred to as soft X-ray beam.

In an absorption contrast method, which uses the difference in transmittance when an X-ray beam transmits a test object, the absorption image acquired in this method exhibits high penetrating power of the X-ray and is put to practical use in internal crack inspection on steel material etc., and security measures, such as baggage inspection.

For a test object that consists of a material having a small density difference, which generates a small contrast due to X-ray absorption, it is effect to use X-ray phase contrast imaging in which a phase shift in the X-ray due to a test object is detected.

As a type of X-ray phase contrast imaging, imaging using an imaging apparatus including a mask that blocks X-ray beams and installed on the edge area of the pixels in the detector unit is disclosed in PTL 1. By setting the apparatus such that an X-ray beam is incident on part of the mask when a test object is not disposed, the positional change of the X-ray due to refraction at the test object can be detected as a change in intensity.

FIGS. 7A and 7B are enlarged views of the detector unit in PTL 1. FIG. 7A is a view of the detector unit in the incident direction of an X-ray beam. FIG. 7B is a view of the detector unit in a direction orthogonal to the incident direction of the X-ray beam.

A shielding element 720 that blocks an X-ray beam is disposed on the edge region of a detection pixel 710 (at the boundary with the adjoin pixel) in the detector unit. An X-ray beam 730 is incident on each pixel such that part of the X-ray beam 730 is incident on the shielding element 720. With such an arrangement, when an X-ray beam is incident on a test object, the position of the incident X-ray beam 730 changes on the detection pixel 710 due to refraction. Since the area of incident X-ray beam blocked by the shielding element 720 changes due to a positional change, the detected intensity of the X-ray beam changes. Therefore, by detecting the changes in the intensity of the X-ray, refraction can be measured.

CITATION LIST

Patent Literature

PTL 1 International Publication No. 2008/029107

SUMMARY OF INVENTION

Technical Problem

PTL 1 has a problem in that when a test object sufficiently absorbs an X-ray beam, the effect of the absorption and information about phase shift due to the test object are mixed and cannot be acquired separately. Specifically, when a change in the intensity of an X-ray beam is detected, it cannot be determined whether the change is due to absorption by the test object or due to a position change in the X-ray beam incident on a shielding element. As a result, the imaging precision of an image associated with phase shift decreases.

Accordingly, the present invention provides an X-ray imaging apparatus and an imaging method capable of acquiring an image associated with phase shift, e.g., a differential phase contrast image or a phase contrast image, in consideration of the X-ray absorption of a test object.

Solution to Problem

An X-ray imaging apparatus according to the present invention includes a splitting element configured to spatially split an X-ray into multiple X-ray beams; a shielding unit including a plurality of shielding elements configured to block part of an X-ray acquired by the splitting element; and a detecting unit including a plurality of pixel groups, each pixel group including a first detection pixel and a second detection pixel, the pixels being configured to detect the intensity of the X-ray beam transmitted through the shielding unit, wherein part of the X-ray beam detected at the first detection pixel is blocked by the shielding elements and the X-ray beam detected at the second detection pixel adjoining the first detection pixel is not blocked by the shielding elements.

An imaging method for an X-ray imaging apparatus according to the present invention includes the steps of blocking part of spatially split X-ray beams by a shielding unit having a plurality of shielding elements; detecting the intensity of the X-ray beams transmitted through the shielding unit by a detecting unit including a plurality of pixel groups, each pixel group including a first detection pixel and a second detection pixel; and detecting an X-ray beam of which part is blocked by the shielding elements by the first detection pixel and detecting an X-ray beam of which part is not blocked by the shielding elements by the second detection pixel adjoining the first detection pixel.

Advantageous Effects of Invention

Accordingly, the present invention provides an X-ray imaging apparatus and an imaging method capable of acquiring an image associated with phase shift, e.g., a differential phase contrast image or a phase contrast image, in consideration of the X-ray absorption of a test object.

DESCRIPTION OF EMBODIMENTS

First Embodiment

Figure 1:
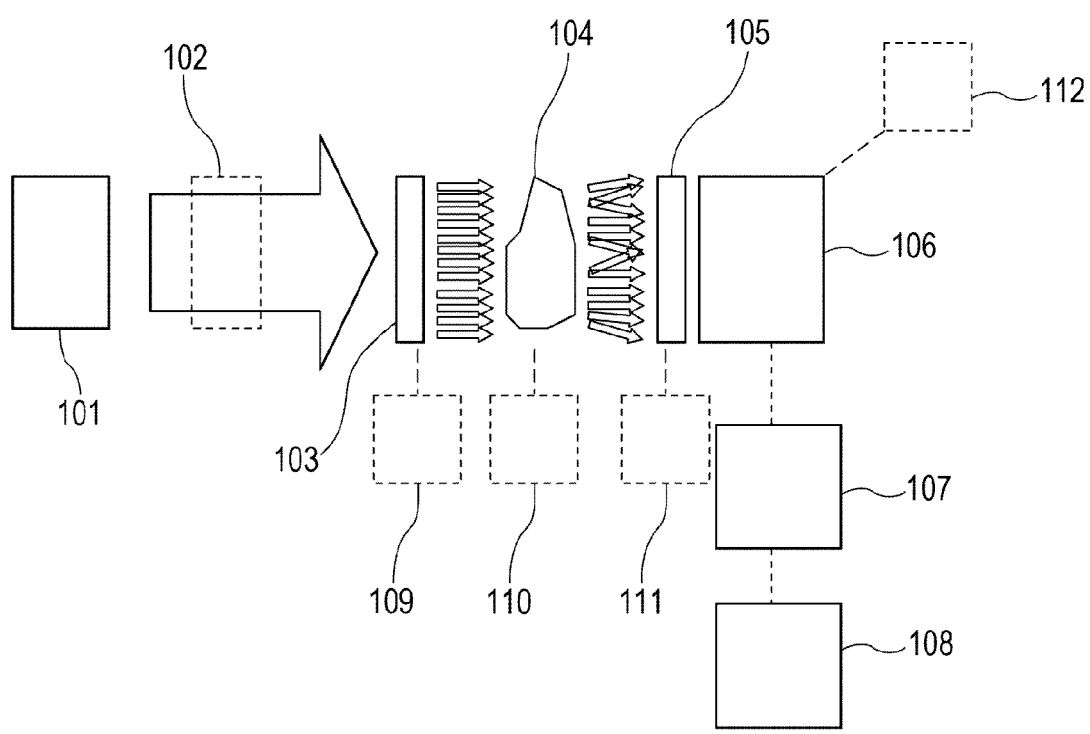
FIG. 1 illustrates the configuration of an X-ray imaging apparatus according to first, second, third, and fourth embodiments.

With reference to FIG. 1, an X-ray imaging apparatus and an imaging method according to this embodiment will be described below. An X-ray generated at an X-ray source 101, which is an X-ray generating unit, is split into, for example, line beams at a splitting element 103.

The splitting element 103 is, for example, a slit array having lines and spaces. The splitting element 103 may be two-dimensional slits or a pinhole array in a direction orthogonal to the split pitch direction. The shape of the slits may be L-shaped or annular or may be a combination of these shapes. The slits in the splitting element 103 may be the same shape or may be different shapes. The slits or pinholes, which are regions transmitting the X-ray, are also referred to as transmitting parts.

The slits in the splitting element 103 do not have to penetrate the substrate of the splitting element 103 so long as they transmit the X-ray. The material of the splitting element 103 may be selected from elements having a high X-ray absorption, such as Pt, Au, Pb, Ta, or W, or may be a compound of these elements.

The X-ray beams acquired through spatial splitting at the splitting element 103 go through a phase shift and are refracted by a test object 104. The X-ray beams are absorbed by the test object 104. The refracted X-ray beams enter a shielding unit 105. The shielding unit 105 includes a plurality of shielding elements.

The intensity of the X-ray beams transmitted through the shielding unit 105 is detected by a detecting unit 106. Information related to the X-ray beams acquired by the detecting unit 106 is numerically processed at a computing unit 107 and is output to a display unit 108, such as a monitor.

The test object 104 may be a human body, an inorganic material, or an organic/inorganic composite. Moving units 109, 110, 111, and 112, such as stepping motors, that move the splitting element 103, the test object 104, the shielding unit 105, and the detecting unit 106, respectively, may be provided. For example, by providing the moving unit 110, the test object 104 can be moved as desired, and an image of a specific site of the test object 104 can be acquired.

The detecting unit 106 can be any type of indirect or direct X-ray detector. For example, the detecting unit 106 may be selected from an X-ray CCD camera, an indirect-conversion-type flat panel detector, and a direct-conversion-type flat panel detector.

The detecting unit 106 may be disposed close to the shielding unit 105 or may be disposed a certain distance apart from the shielding unit 105. The shielding unit 105 may be integrated in the detecting unit 106.

When monochromatic X-ray is used, a monochromatizing unit 102 may be disposed between the X-ray source 101 and the splitting element 103. The monochromatizing unit 102 may be a monochrometer or an X-ray multilayer mirror combined with slits.

To prevent image obscuration due to X-rays scattering from the test object 104, a grid, which is used in diagnostic X-ray system, may be disposed between the test object 104 and the shielding unit 105.

Figure 2A:
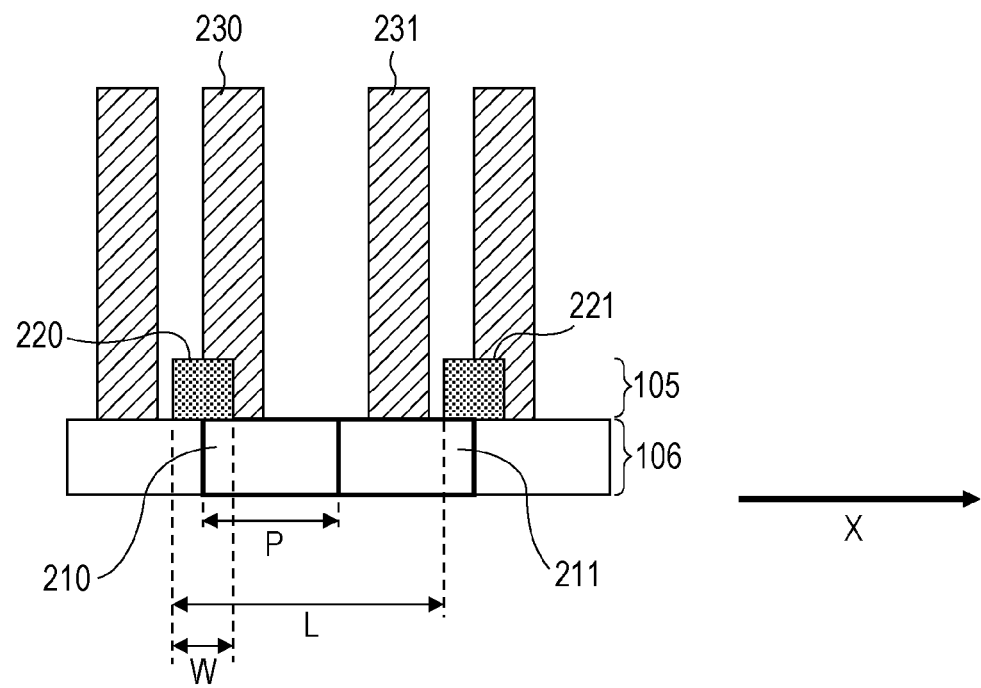
FIGS. 2A and 2B illustrate a shielding unit according to the first embodiment.
Figure 2B:
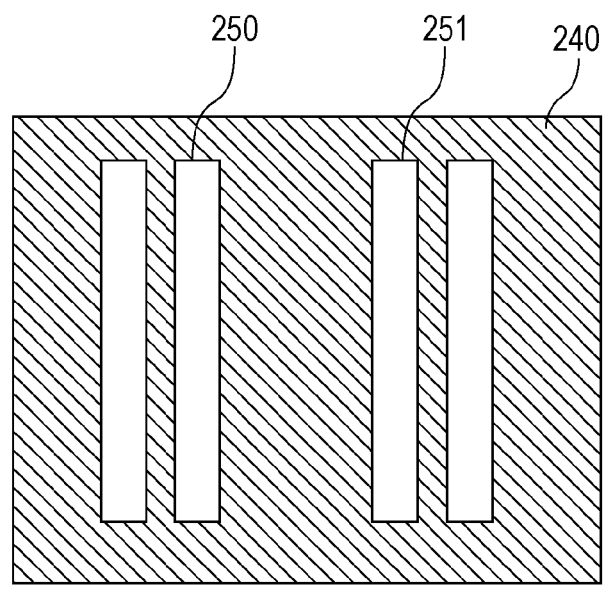

With reference to FIGS. 2A and 2B, the shielding unit 105 according to this embodiment will be described in detail. In FIG. 2A, the shielding unit 105 includes shielding elements 220 and 221, having a width of W, are disposed on the detecting unit 106 at a pitch L. The detecting unit 106 includes a plurality of pixel groups, which each includes a detection pixel 210, which is a first detection pixel, and a detection pixel 211, which is a second detection pixel. The shielding elements 220 and 221 may be selected from elements having a high X-ray absorption, such as Pt, Au, Pb, Ta, or W. The shielding elements 220 and 221 do not have to complete absorb the incident X-ray beams but may transmit part of the X-ray beams.

The pitch L of the shielding elements 220 and 221 is equal to 2P (L=2P), where P represents the size of the detection pixels 210 and 211. The shielding element 220 is disposed at the boundary (edge region) between the detection pixel 210 and the adjoining pixel on the left. The shielding element 221 is disposed at the edge region between the detection pixel 211 and the adjoining pixel on the right.

In FIG. 2A, the shielding unit 105 and the detecting unit 106 are integrated. When the shielding unit 105 is disposed a certain distance apart from the detecting unit 106, the pitch L of the shielding elements 220 and 221 is 2P/M, where M represents the projection magnitude of the shielding unit 105 to the detecting unit 106, and the shielding unit 105 and the detecting unit 106 are arranged such that the shadows of the shielding elements are projected on the edge regions of the detection pixels.

Part of an X-ray beam 230 is incident on the shielding element 220, whereas an X-ray beam 231 is not incident on the shielding element 221.

FIG. 2B illustrates the example configuration of the splitting element 103. A splitting element 240 includes slits 250 and 251, which are transmitting parts. An X-ray beam that transmits the slit 250 is the X-ray beam 230, and an X-ray beam that transmits the slit 251 is the X-ray beam 231. The width and pitch of the slits are set appropriately in consideration of the X-ray divergence angle, the X-ray width on a detection pixel, and so on.

By arranging the splitting element 240, the shielding elements 220 and 221, and the detection pixels in this way, the intensity of the X-ray beam 231 detected by the detection pixel 211 changes due to the absorption of the test object 104. The intensity of the X-ray beam 230 detected by the detection pixel 210 changes due to the absorption of the test object 104 and the positional change caused by refraction. Specifically, an image (absorption image) corresponding to the X-ray transmittance of the test object 104 and an image (phase contrast image) corresponding to the displacement of the X-ray beam due to a phase shift can be acquired on the basis of changes in the intensity of the X-ray beams 230 and 231 detected by the detection pixels 210 and 211, respectively.

The detected intensity I of the X-ray beam 231 when the test object 104 is disposed and the detected intensity $I_O$ when the test object 104 is not disposed can be represented by Expression 1.

[Math. 1]

$$\frac{I}{I_0} = T \tag{1}$$

where T represents transmittance. Transmittance can be determined from the intensity data acquired with and without the test object 104.

The detected intensity of the X-ray beam 230 can be determined by Expression 2 if the detected intensity changes linearly with respect to the minute positional change $\Delta X$ in the X direction.

$$\Delta X = aI_O + b \tag{2}$$

where a and b are coefficients. The a and b can be determined by measuring the intensity $I_O$ without the test object 104 while moving the splitting element 103 and substituting the measured data to Expression 2. The displacement $\Delta X$ at each point on the test object 104 can be determined by substituting Expression 1 into Expression 2.

In this case, since two different data sets about the X-ray beam 230 incident on a shielding element and the X-ray beam 231 not incident on a shielding element are acquired, the spatial resolution in the X direction is ½.

In addition to the above-described measurement, the same measurement is performed by after moving the splitting element 103, the shielding unit 105, the detecting unit 106, or the test object 104 in the X direction by the moving unit 109, 111, 112, or 110, respectively. In this way, the spatial resolution can be improved.

Figure 3:
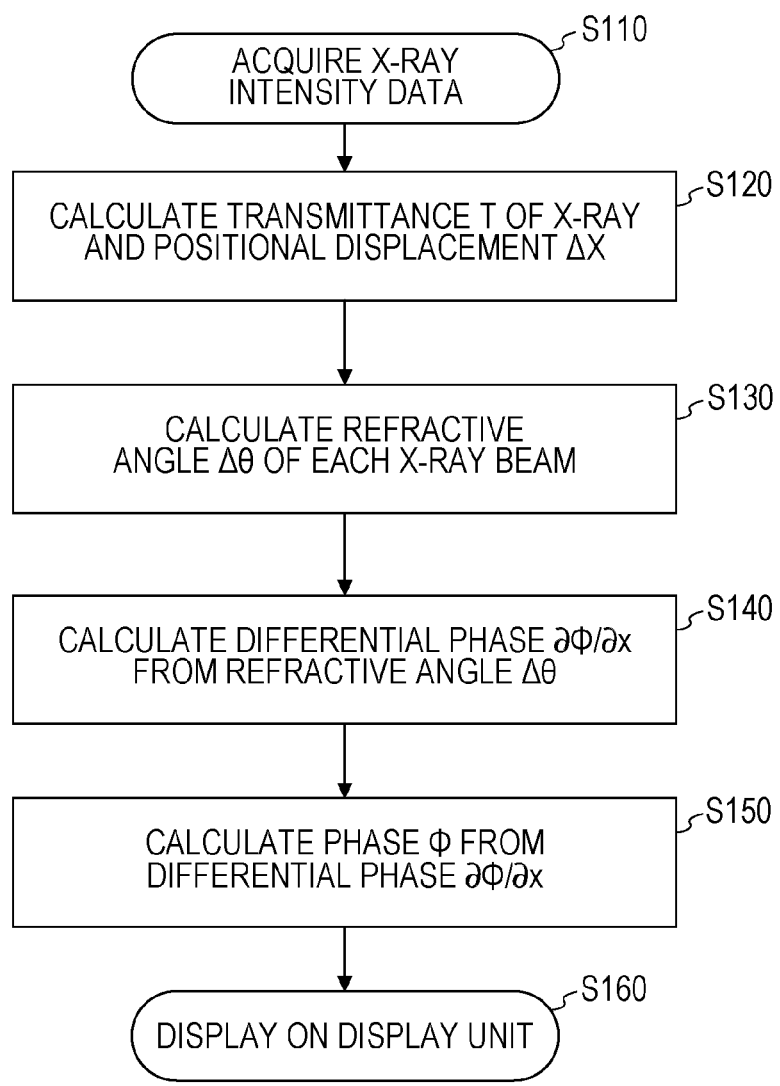
FIG. 3 illustrates a processing flow of a computing unit according to the first embodiment.

FIG. 3 is a flow chart illustrating the computation performed at the computing unit 107. First, intensity data for each X-ray beam is acquired (S110). Then, X-ray transmittance (T) is calculated from the detected intensity of X-ray beam not incident on a shielding element. Using Expression 2, the positional change ($\Delta X$) of the X-ray is determined on the basis of the X-ray transmittance (T) and the detected intensity (I) of the X-ray beam partially incident on the shielding element (S120).

Next, the refraction angle ($\Delta \theta$) of each X-ray is calculated using Expression 3 (S130).

[Math. 2]

$$\Delta \theta = \tan^{-1}\left(\frac{\Delta X}{Z}\right) \quad (3)$$

where Z represents the distance between the test object 104 and the shielding unit 105.

Next, the differential phase ($\partial \phi / \partial X$) of an X-ray beam is calculated using Expression 4 (S140).

[Math. 3]

$$\frac{\partial \phi}{\partial X} = \frac{2\pi}{\lambda} \Delta \theta \quad (4)$$

where $\lambda$ represents the wavelength of the X-ray beam and represents an effective wavelength when a continuous X-ray beam is used.

Next, the phase ($\phi$) is calculated by integrating the acquired differential phases ($\partial \phi / \partial X$) in the X direction (S150).

The computing unit 107 outputs a transmittance image (distribution of T), a positional change image (distribution of $\Delta X$), a differential phase contrast image (distribution of $\partial \phi / \partial X$), and a phase contrast image (distribution of $\phi$), which are calculated as described above, to the display unit 108 (S160).

The transmittance image, the phase contrast image, and so on may be displayed adjacent to each other or may be displayed individually on display unit 108.

According to this embodiment, the effect of the X-ray being absorbed by the test object 104 and the effect of the phase shift can be separated. Therefore, an X-ray imaging apparatus and an imaging method capable of acquiring a differential phase contrast image, a phase contrast image, etc., in consideration of the X-ray absorption of the test object can be provided.

In the first embodiment, the shielding elements are disposed between pixels. However, the shielding elements do not necessarily have to be disposed on the edge regions of the pixels.

The first detection pixel and the second detection pixel may each be multiple pixels.

Second Embodiment

Figure 4A:
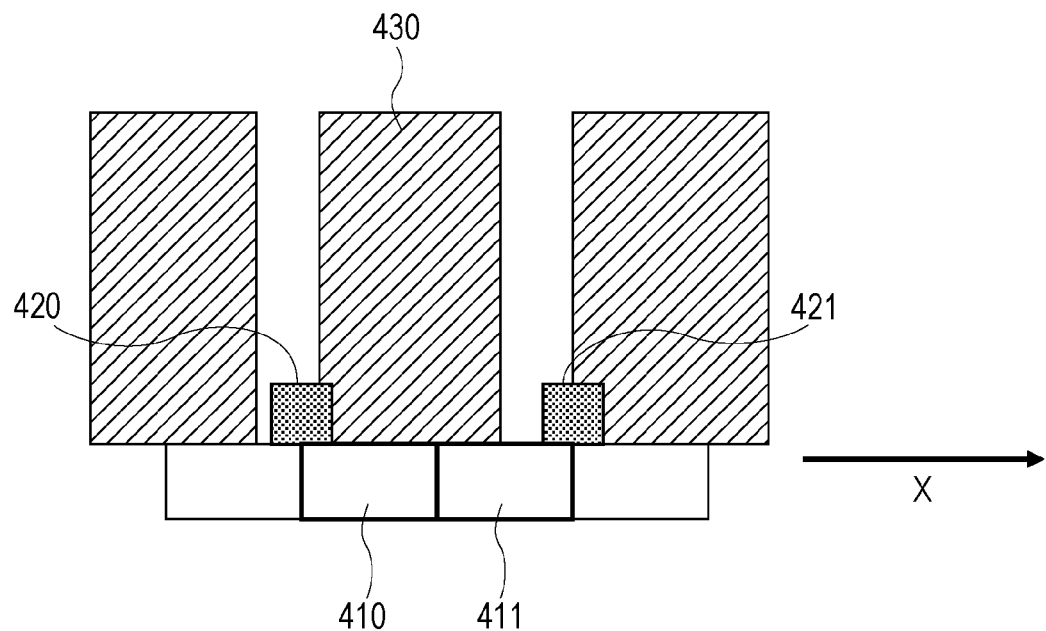
FIGS. 4A and 4B illustrates the configuration of a shielding unit according to the second embodiment.

In FIG. 4A, the positional relationship of detection pixels 410 and 411 and shielding elements 420 and 421 is the same as that in the first embodiment. However, the positional relationship of an incident X-ray beam 430 with respect to the detection pixels 410 and 411 differs from that in the first embodiment. That is, in this embodiment, the X-ray beam 430 is incident on the area between the shielding element 420 and the shielding element 421.

Figure 4B:
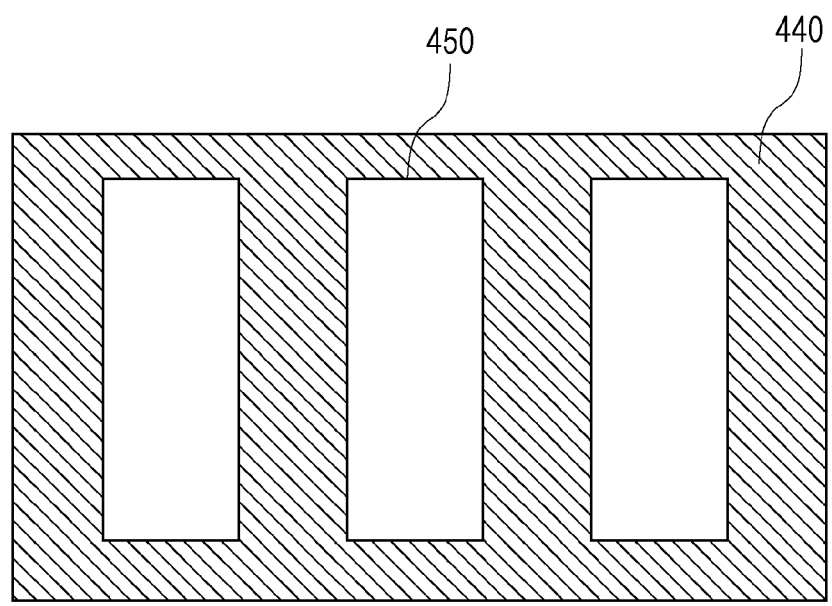

FIG. 4B illustrates a splitting element 440. The splitting element 440 includes a slit 450, which is a transmitting part. An X-ray beam that transmits through the slit 450 is emitted as the X-ray beam 430 illustrated in the drawing. Part of the X-ray beam 430 is blocked in the X direction by the shielding element 420 and is incident on the detection pixels 410 and 411.

By arranging the splitting element 440, the shielding element 420, and the detection pixels 410 and 411 in this way, the intensity of the X-ray beam 430 detected by the detection pixels 410 and 411 changes due to the absorption of the test object 104. The intensity detected by the detection pixels 410 and 411 changes due to the positional change of the X-ray beam 430 caused by refraction by the test object 104.

The change in the detected intensity due to absorption is the same in the detection pixels 410 and 411. The change in the detected intensity due to positional change differs in the detection pixels 410 and 411. For example, when a change in the detected intensity due to the positional change occurs linearly, the positional change corresponding to the changes of intensity detected by the detection pixels 410 and 411 can be represented by Expressions 5 and 6.

[Math. 4]

$$\Delta X = a\frac{I_{410}}{T} + b \quad (5)$$

[Math. 5]

$$\Delta X = c\frac{I_{411}}{T} + d \quad (6)$$

where $I_{410}$ and $I_{411}$ represent the intensities detected by the detection pixels 410 and 411 and T represents the X-ray transmittance of the test object 104. Specifically, by measuring the intensities $I_{410}$ and $I_{411}$ while moving the splitting element 103 without the test object 104 disposed and substituting the measured data to Expressions 5 and 6, coefficients a, b, c, and d are determined. When the test object 104 is measured, the X-ray transmittance T and the displacement $\Delta X$ can be determined by solving the simultaneous equations.

The computation flow is the same as that according to the first embodiment and is illustrated in FIG. 3. According to this embodiment, the effect of the X-ray absorption of the test object and the effect of the phase shift can be separated. Therefore, an X-ray imaging apparatus and an imaging method capable of acquiring a differential phase contrast image, a phase contrast image, etc., in consideration of the X-ray absorption of the test object can be provided.

Third Embodiment

Figure 5A:
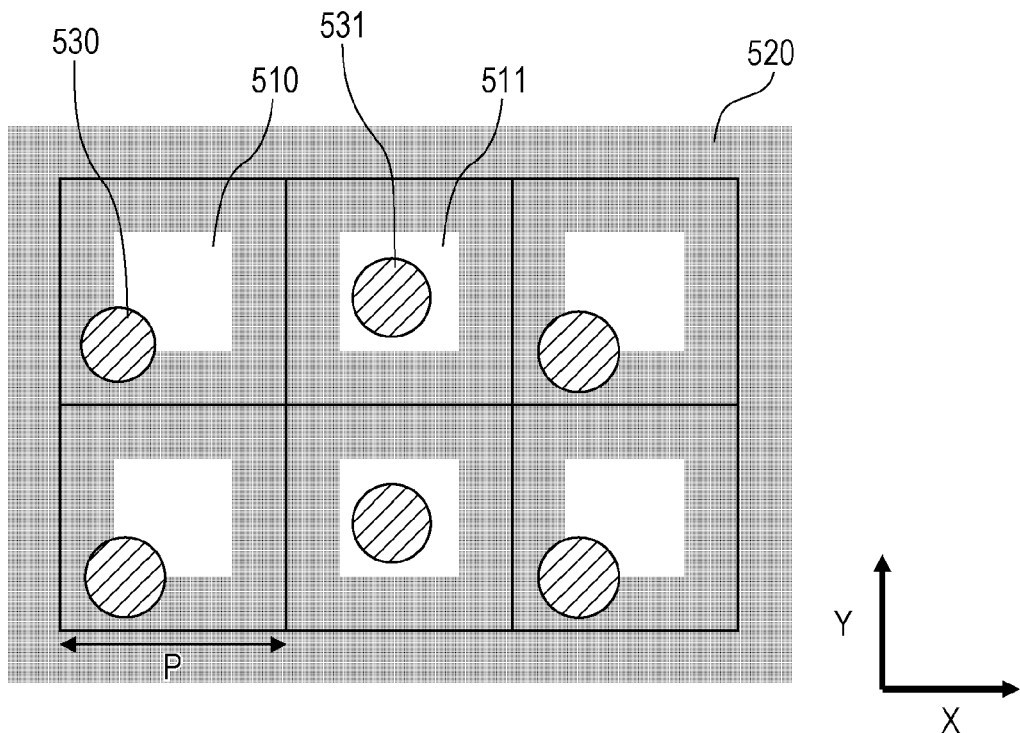
FIG. 5 illustrate the configuration of a shielding unit according to the third embodiment.

The two-dimensional arrangement according to this embodiment will be described. FIG. 5A is a view from the incident direction of an X-ray beam. Shielding elements 520 are disposed on the edge regions of the detection pixels 510 and 511. The pitch of the shielding elements 520 is P, which is equal to the length of one side of a detection pixel.

Figure 5B:
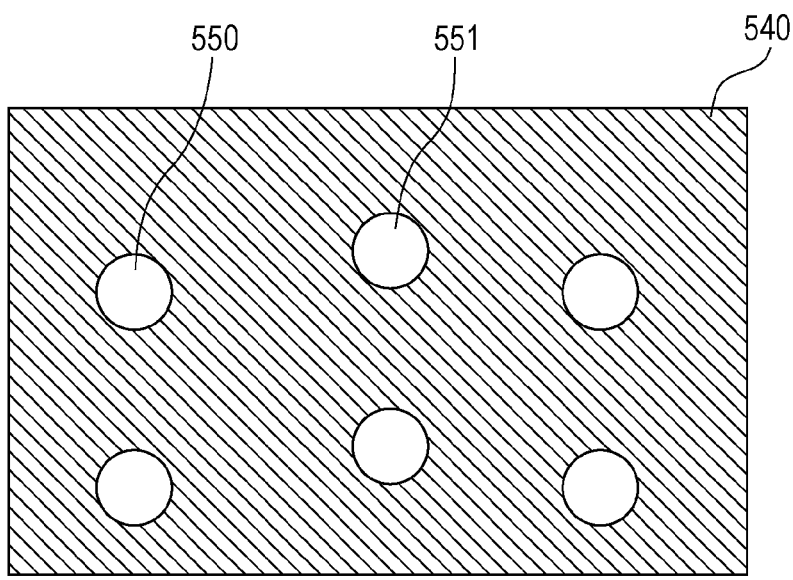

FIG. 5B illustrates the configuration of a splitting element 540. The splitting element 540 has pinholes 550 and 551. The X-ray transmitted through the pinhole 550 is an X-ray beam 530, and the X-ray transmitted through the pinhole 551 is an X-ray beam 531.

The incident position of the X-ray beam 530 is set such that part of the X-ray beam 530 is blocked by the shielding element 520. By changing the incident position of the X-ray beam 530, the intensity of the X-ray beam 530 detected at the detection pixel 510 changes. In this case, the intensity changes not only when the displacement of the incident position is in the X direction but also in the Y direction.

The incident position of the X-ray beam 531 is set to the center part of the detection pixel 511 such that the X-ray beam 531 is not blocked by the shielding element 520. Therefore, the intensity detected by the detection pixel 511 changes only by the absorption of the test object 104. Accordingly, the transmittance T of the test object 104 can be determined by the detection pixel 511. By using the determined transmittance T, the positional change of the X-ray beam 531 can be accurately determined from the intensity detected by the detection pixel 511. The center part of the detection pixel 511 does not have to be exactly at the center of the detection pixel 511 so long as the transmittance T can be calculated.

As illustrated in FIG. 5A, when detection pixels not shielded by the shielding elements are arranged in a first direction (e.g., Y direction) and in a second direction (e.g., X direction) orthogonal to the first direction, the splitting element is configured as illustrated in FIG. 5B. Specifically, the pinholes, which are transmitting parts, of the splitting element are linearly aligned in the first direction but arranged in a zigzag pattern in the second direction.

Figure 6A:
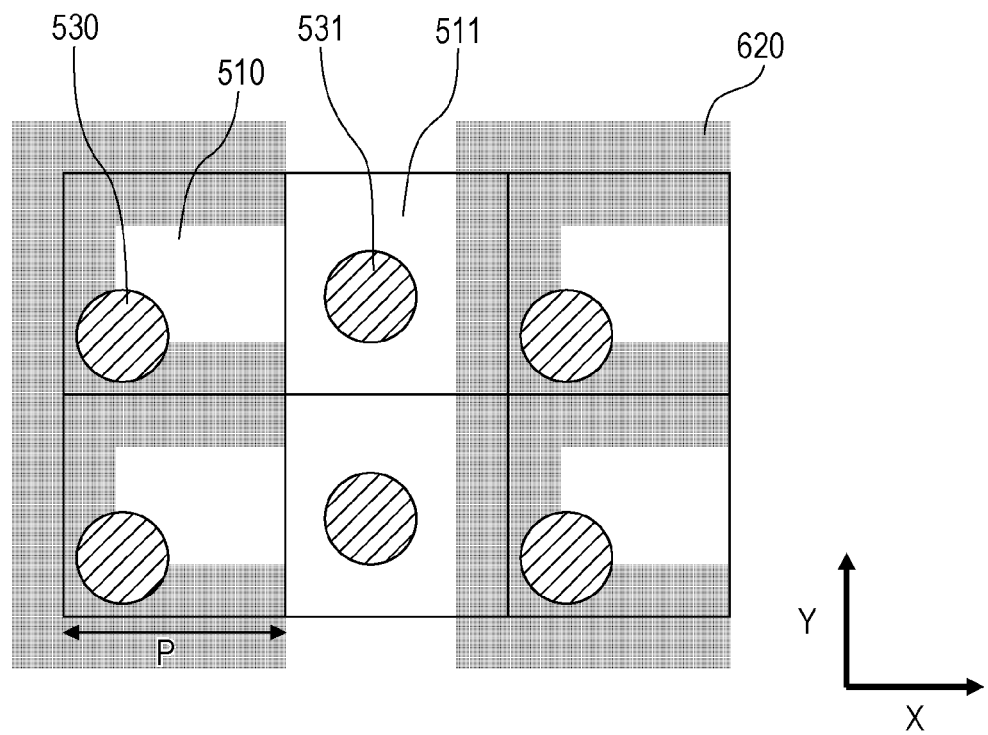
FIGS. 6A and 6B illustrates the configuration of the shielding unit according to the third embodiment.

FIG. 6A illustrates a variation of FIG. 5A. To prevent part of the X-ray beam 531 from being blocked by a shielding element 620 even when the incident position of the X-ray beam 531 used for determining the X-ray transmittance of the test object 104 changes, the size of the shielding element 620 is reduced, and space for the detection pixel 511 is increased.

Figure 6B:
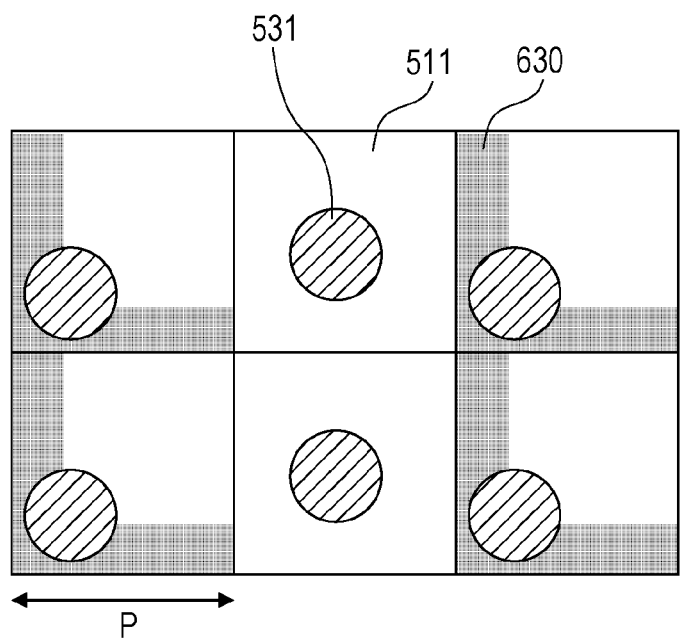
Figure 7A:
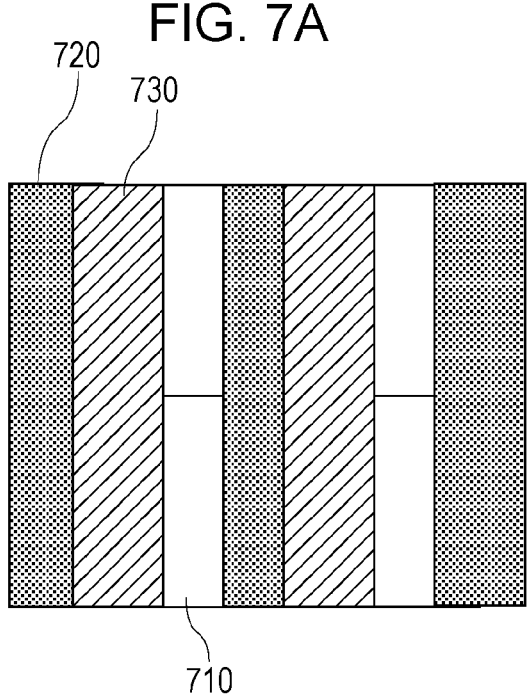
FIGS. 7A and 7B illustrate the configuration of an X-ray imaging apparatus according to PTL 1.
Figure 7B:
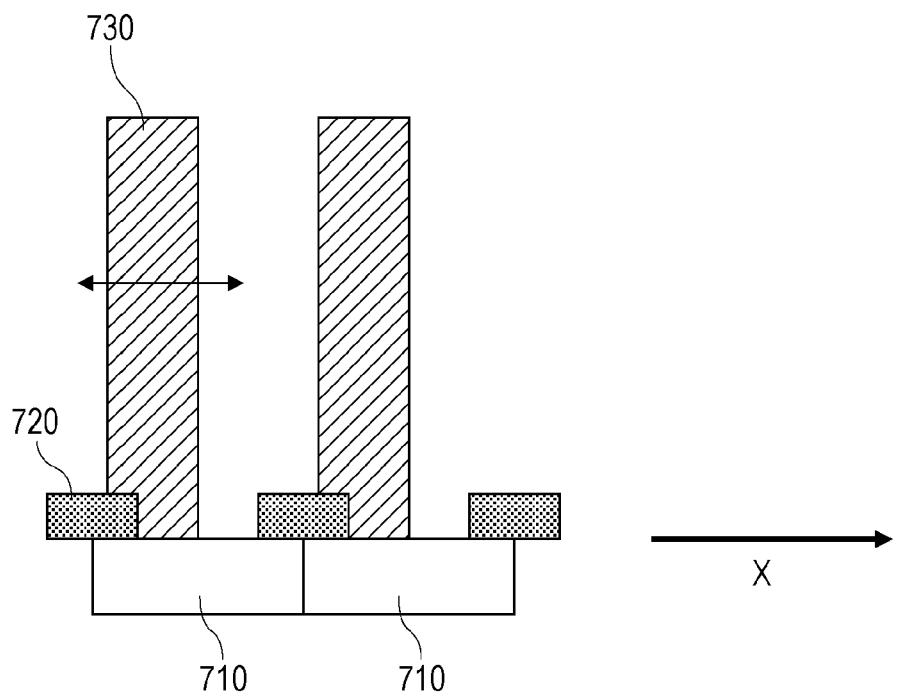

FIG. 6B illustrates the shielding element 630 set smaller than that illustrated in FIG. 6A and not disposed on the detection pixel 511. In this way, the shielding element 630 can be disposed on the edge regions of the pixels.

As described above, a transmittance image (distribution of T) can be calculated from the intensity detected by the detection pixel 511. By calculating the intensity detected by the detection pixel 510 using the intensity detected by the detection pixel 511, an image associated with the change in X-ray intensity with respect to the phase shift can be calculated. These images can be displayed on the display unit 108.

According to this embodiment, the effect of the X-ray absorption of the test object and the effect of the phase shift can be separated. Therefore, an X-ray imaging apparatus and an imaging method capable of acquiring a differential phase contrast image, a phase contrast image, etc., in consideration of the X-ray absorption of the test object can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-158133, filed Jul. 12, 2010, which is hereby incorporated by reference herein in its entirety.

REFERENCE SIGNS LIST

101 X-ray source
102 monochromatizing unit
103 splitting element
104 test object
105 shielding unit
106 detecting unit
107 computing unit
108 display unit

The invention claimed is:

1. An X-ray imaging apparatus comprising:
   a splitting element configured to spatially split an X-ray into multiple X-ray beams;
   a shielding unit including a shielding elements configured to block part of an X-ray acquired by the splitting element;
   a detecting unit including a pixel group, the pixel group including a first detection pixel and a second detection pixel, the pixels being configured to detect the intensity of the X-ray beam transmitted through the shielding unit; and
   a computing unit configured to compute X-ray transmittance of a test object on the basis of the intensity of the X-ray detected by the second detection pixel,
   wherein part of the X-ray beam detected at the first detection pixel is blocked by the shielding elements and the X-ray beam detected at the second detection pixel adjoining the first detection pixel is not blocked by the shielding element.

2. The X-ray imaging apparatus according to claim 1, wherein the shielding element is not disposed on the boundary between the first detection pixel and the second detection pixel.

3. The X-ray imaging apparatus according to claim 1, wherein the X-ray beam incident on the first detection pixel and the X-ray beam incident on the second detection pixel are split.

4. The X-ray imaging apparatus according to claim 1, wherein the X-ray beam incident on the first detection pixel and the X-ray beam incident on the second detection pixel are not split.

5. The X-ray imaging apparatus according to claim 1, wherein,
   the detection pixels not blocked by the shielding elements are linearly aligned in a first direction and a second direction orthogonal to the first direction, and
   transmitting parts of the splitting element are linearly aligned in the first direction and disposed in a zigzag pattern in the second direction.

6. An X-ray imaging apparatus according to claim 1,
   wherein the positions of X-ray beams incident on the first detection pixels differ from the positions X-ray beams incident on the second detection pixels, and part of the X-ray beams incident on the first detection pixels is blocked by the shielding elements.

7. The X-ray imaging apparatus according to claim 1, wherein the first detection pixels include a region that is shielded from the X-ray beams by the shielding elements and a region that the X-ray beams are allowed to enter, and a dividing line between the region that is shielded from the X-ray beams and the region that the X-ray beams are allowed to enter is arranged not obliquely.

8. The X-ray imaging apparatus according to claim 1, wherein the detecting unit includes a plurality of pixel groups.

9. The X-ray imaging apparatus according to claim 8, wherein the computing unit computes an image of the test object associated with a phase shift of the X-ray beams based intensities of the X-ray beams detected at the first detection pixel and the second detection pixel.

10. An imaging method for an X-ray imaging apparatus, comprising the steps of:
    blocking part of spatially split X-ray beams by a shielding unit having a shielding elements;
    detecting the intensity of the X-ray beams transmitted through the shielding unit by a detecting unit including a pixel group, the pixel group including a first detection pixel and a second detection pixel;
    detecting an X-ray beam of which part is blocked by the shielding elements by the first detection pixel and detecting an X-ray beam of which part is not blocked by the shielding elements by the second detection pixel adjoining the first detection pixel; and
    calculating X-ray transmittance of a test object on the basis of the intensity an X-ray beam detected by the second detection pixel.

11. The imaging method according to claim 10, further comprising a step of:
    computing a differential phase contrast image or a phase contrast image of the test object on the basis of the intensities of X-ray beam detected by the first detection pixel and the second detection pixel.

12. The imaging method according to claim 10, wherein the first detection pixels include a region that is shielded from the X-ray beams by the shielding elements and a region that the X-ray beams are allowed to enter, and a dividing line between the region that is shielded from the X-ray beams and the region that the X-ray beams are allowed to enter is arranged not obliquely.

13. The imaging method according to claim 10, wherein the detecting unit includes a plurality of pixel groups.

14. An X-ray imaging apparatus comprising:
    a splitting element configured to spatially split an X-ray;
    a shielding unit including a plurality of shielding element configured to block part of X-ray beams acquired by the splitting element; and
    a detecting unit including a plurality of pixel groups, each pixel group including a first detection pixel and a second detection pixel, the pixels being configured to detect the intensity of the X-ray beam transmitted through the shielding unit; and
    a computing unit configured to compute X-ray transmittance of a test object on the basis of the intensity of the X-ray detected by the second detection pixel,
    wherein the shielding elements are disposed on the first detection pixel and are not disposed on the second detection pixel.

15. The X-ray imaging apparatus according to claim 14, wherein the first detection pixels include a region that is shielded from the X-ray beams by the shielding elements and a region that the X-ray beams are allowed to enter, and a dividing line between the region that is shielded from the X-ray beams and the region that the X-ray beams are allowed to enter is arranged not obliquely.

16. An X-ray imaging apparatus comprising:
    a splitting element configured to spatially split an X-ray into multiple X-ray beams;
    a shielding unit including a plurality of shielding elements configured to block part of an X-ray acquired by the splitting element; and
    a detecting unit including a plurality of pixel groups, each pixel group including a first detection pixel and a second detection pixel, the pixels being configured to detect the intensity of the X-ray beam transmitted through the shielding unit,
    wherein part of the X-ray beam detected at the first detection pixel is blocked by the shielding elements and the X-ray beam detected at the second detection pixel adjoining the first detection pixel is not blocked by the shielding elements, and
    wherein, among the plurality of pixel groups, a first detection pixel and a second detection pixel included in each pixel group are alternately arranged in the detecting unit in one or more directions.

* * * * *